United States Patent
Kato (10) Patent No.: US 12,097,078 B2
(45) Date of Patent: Sep. 24, 2024

(54) PROGRAM AND ULTRASONIC IMAGE DISPLAY SYSTEM

(71) Applicant: GE Precision Healthcare LLC, Wauwatosa, WI (US)

(72) Inventor: Hanako Kato, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 316 days.

(21) Appl. No.: 17/501,696

(22) Filed: Oct. 14, 2021

(65) Prior Publication Data

US 2022/0125415 A1  Apr. 28, 2022

(30) Foreign Application Priority Data

Oct. 27, 2020 (JP) .................................. 2020-179977

(51) Int. Cl.
*A61B 8/00* (2006.01)
*G06F 3/0484* (2022.01)
*G06F 3/16* (2006.01)

(52) U.S. Cl.
CPC ................ *A61B 8/54* (2013.01); *A61B 8/463* (2013.01); *A61B 8/467* (2013.01); *G06F 3/0484* (2013.01); *G06F 3/165* (2013.01)

(58) Field of Classification Search
CPC ........... A61B 8/54; A61B 8/463; A61B 8/467; G06F 3/0484; G06F 3/165
See application file for complete search history.

(56) References Cited

U.S. PATENT DOCUMENTS

| 6,656,136 | B1 * | 12/2003 | Weng | A61N 7/02 600/407 |
| 2013/0216114 | A1 * | 8/2013 | Courtney | A61B 8/12 382/128 |
| 2015/0038846 | A1 * | 2/2015 | Abe | A61B 8/467 600/443 |
| 2016/0015367 | A1 * | 1/2016 | Schneider | A61B 8/0883 600/437 |

FOREIGN PATENT DOCUMENTS

| JP | 2018057698 A | * | 4/2018 |
| JP | 2018061659 A |   | 4/2018 |

OTHER PUBLICATIONS

JP application 2020-179977 filed Oct. 27, 2020—Office Action issued Dec. 14, 2021, English Machine Translation; 3 pages.
(Continued)

*Primary Examiner* — Isam A Alsomiri
*Assistant Examiner* — Abdallah Abulaban (57) ABSTRACT

An ultrasonic image display system and a program for controlling an ultrasonic image display system are disclosed herein. The ultrasonic image display system includes at least one processor and memory. In the memory is stored at least one protocol including a plurality of image acquisition steps. The processor is adapted to load the protocol to start a first run of the protocol, interrupt the first run of the protocol, acquire data for a second ultrasonic image of the patient and store the data in the memory after interrupting the first run of the protocol at one of the acquisition steps. The processor is adapted to interrupt the second run of the protocol at the same one of the acquisition steps or give notice that the second run of the protocol will be interrupted at the same one of the acquisition steps.

13 Claims, 7 Drawing Sheets

(56) References Cited

OTHER PUBLICATIONS

JP2018-057698A English Abstract; Espacenet.com May 26, 2022; 1 page.
JP2018-061659A English Abstract; Espacenet.com May 26, 2022; 1 page.

* cited by examiner

PROGRAM AND ULTRASONIC IMAGE DISPLAY SYSTEM

CROSS-REFERENCE TO RELATED APPLICATIONS

This application claims priority based on Japanese Patent Application No. 2020-179977, filed on Oct. 27, 2020, the contents of which are incorporated herein by reference.

FIELD

The present invention relates to an ultrasonic image display system for acquiring data for ultrasonic images following a plurality of ultrasonic image acquisition steps defined by a protocol, and a program for controlling the same.

BACKGROUND

In an examination using an ultrasonic diagnostic apparatus, which is an example of ultrasonic image display systems, a plurality of ultrasonic images are sometimes acquired via a plurality of image acquisition steps defined by a protocol. The protocol defines conditions for ultrasound transmission/reception, conditions for ultrasonic image production, etc. used at each of the plurality of image acquisition steps, and is created and stored before performing the examination. In the examination, the created protocol is loaded, and ultrasound transmission/reception and ultrasonic image production are performed always in a defined order and with defined conditions following the protocol. Such an examination following a protocol is performed in routine examinations in many cases.

BRIEF SUMMARY

In an embodiment, an ultrasonic image display system includes at least one processor and memory. In the memory, there is stored at least one protocol including a plurality of image acquisition steps, each of which defines conditions for acquiring a first ultrasonic image of a patient. The processor is adapted to perform control including the acts of: loading the protocol from the memory to start a first run of the protocol on the patient; after starting the first run of the protocol, interrupting the first run of the protocol at one of said plurality of image acquisition steps; after interruption of the first run of the protocol, acquiring data for a second ultrasonic image of the patient and storing the data in the memory, and moreover storing in said memory information indicating that the first run of the protocol is interrupted at the specific one of the plurality of image acquisition steps; after resuming the first run of the protocol and completing said run, and when starting a second run of the protocol on the patient, loading the information from the memory; and giving notice that the second run of the protocol will be interrupted at the same image acquisition step as that specified by the information.

In in embodiment, an ultrasonic image display system including at least one processor, memory, and a display. In the memory is stored at least one protocol including a plurality of image acquisition steps, each of which defines conditions for acquiring a first ultrasonic image of a patient. The processor is adapted to perform control including the acts of: loading the protocol from the memory to start a first run of the protocol on the patient; after starting the first run of the protocol, interrupting the first run of the protocol at one of said plurality of image acquisition steps; after interruption of the first run of the protocol, acquiring data for a second ultrasonic image of the patient and storing the data in the memory, and storing in the memory information indicating that the first run of the protocol is interrupted at the specific one of the plurality of image acquisition steps, and moreover the information specifying the second ultrasonic image; after resuming the first run of the protocol and completing the run, and when starting a second run of the protocol on the patient, loading the information from the memory; interrupting the second run of the protocol at the image acquisition step specified by the information; and loading from the memory the data for the second ultrasonic image specified by said information and displaying the second ultrasonic image on the display after interruption of the second run.

A program for controlling an ultrasonic image display system including at least one processor, and memory. In the memory is stored at least one protocol including a plurality of image acquisition steps, each of which defines conditions for acquiring a first ultrasonic image of a patient. The program for controlling causes the processor to perform control including the acts of: loading the protocol from the memory to start a first run of the protocol on the patient; after starting the first run of the protocol, interrupting the first run of the protocol at one of the plurality of image acquisition steps; after interruption fo the first run of the protocol, acquiring data for a second ultrasonic image of the patient and storing the data in the memory, and moreover storing in the memory information indicating that the first run of the protocol is interrupted at the specific one of the plurality of image acquisition steps; after resuming the first run of the protocol and completing the run, and when starting a second run of the protocol on the patient, loading the information from the memory, and giving notice that the second run of the protocol will be interrupted at the same image acquisition step as that specified by the information.

DETAILED DESCRIPTION

Embodiments of the present disclosure will now be described, by way of example, with reference to the Figures. In the following embodiments will be described a case in which an ultrasonic image display system is constructed from an ultrasonic image display apparatus. The ultrasonic image display apparatus is an ultrasonic diagnostic apparatus, for example.

Figure 1:
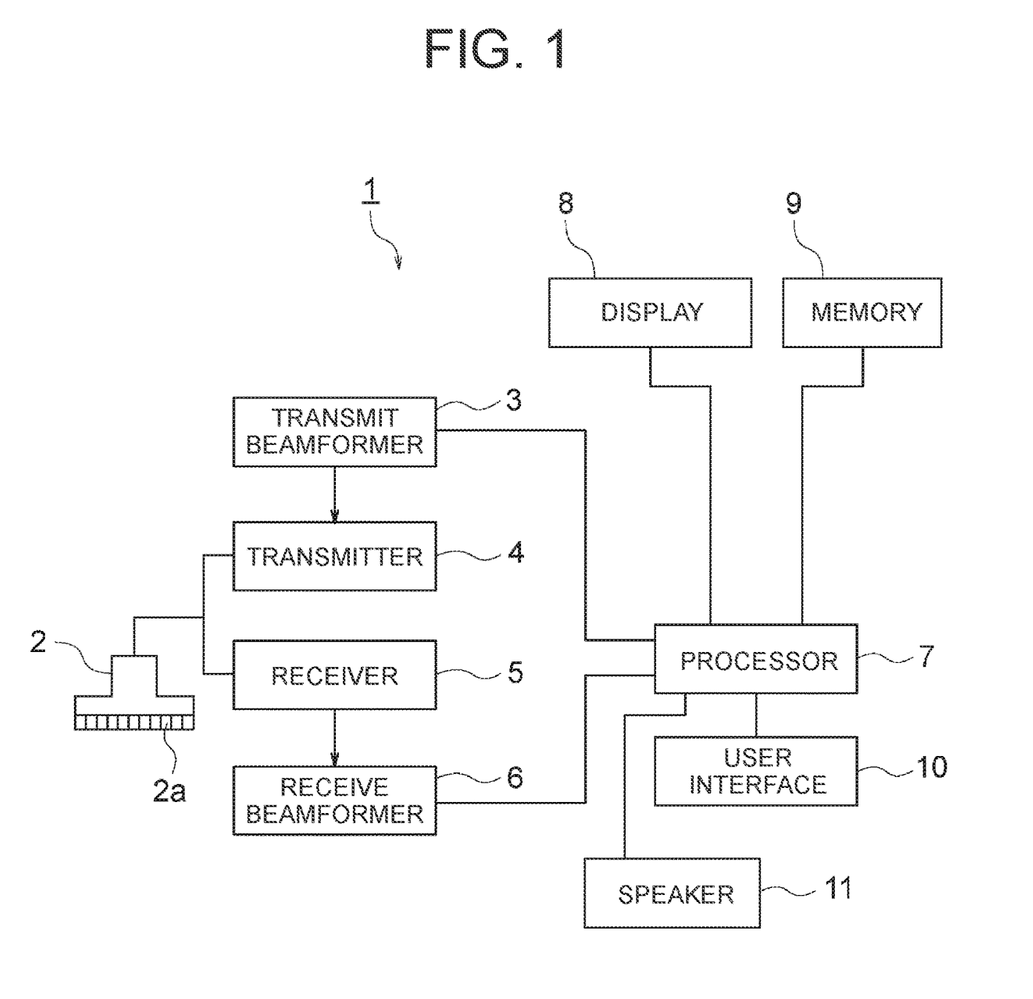
FIG. 1 is a block diagram showing an ultrasonic image display apparatus, which is an example of the ultrasonic image display system in accordance with an embodiment.

An ultrasonic image display apparatus 1 shown in FIG. 1 comprises an ultrasonic probe 2, a transmit beamformer 3, and a transmitter 4. The ultrasonic probe 2 performs an ultrasonic scan on a patient, and receives ultrasonic echoes. More specifically, the ultrasonic probe 2 has a plurality of vibration elements 2a for emitting pulsed ultrasound to the patient (not shown). The plurality of vibration elements 2a are driven by the transmit beamformer 3 and transmitter 4 to emit pulsed ultrasound.

The ultrasonic image display apparatus 1 further comprises a receiver 5 and a receive beamformer 6. The pulsed ultrasound emitted from the vibration elements 2a is reflected in the inside of the patient to generate echoes returning to the vibration elements 2a. The echoes are converted into electrical signals by the vibration elements 2a, which are echo signals, and are input to the receiver 5. The echo signals undergo amplification, etc. with a required gain at the receiver 5, and then input to the receive beamformer 6, where receive beamforming is performed. The receive beamformer 6 outputs receive-beamformed ultrasound data.

The receive beamformer 6 may be a hardware beamformer or a software beamformer. In the case that the receive beamformer 6 is a software beamformer, it may comprise one or more processors including a graphics processing unit (GPU), a microprocessor, a central processing unit (CPU), a digital signal processor (DSP), or any one or more of other kinds of processors capable of executing logical operations. The processor(s) constituting the receive beamformer 6 may be constructed from a processor separate from a processor 7, which will be described later, or constructed from the processor 7.

The ultrasonic probe 2 may comprise electrical circuitry to perform all or part of transmit and/or receive beamforming. For example, all or part of the transmit beamformer 3, transmitter 4, receiver 5, and receive beamformer 6 may be situated within the ultrasonic probe 2.

The ultrasonic image display apparatus 1 also comprises the processor 7 for controlling the transmit beamformer 3, transmitter 4, receiver 5, and receive beamformer 6. Moreover, the ultrasonic image display apparatus 1 comprises a display 8, memory 9, a user interface 10, and a speaker 11.

The processor 7 comprises one or more processors. The processor 7 is in electronic communication with the ultrasonic probe 2. The processor 7 may control the ultrasonic probe 2 to acquire ultrasound data. The processor 7 controls which of the vibration elements 2a are active, and the shape of an ultrasonic beam transmitted from the ultrasonic probe 2. The processor 7 is also in electronic communication with the display 8, and the processor 7 may process the ultrasound data into ultrasonic images for display on the display 8. The phrase "electronic communication" may be defined to include both wired and wireless connections. The processor 7 may include a central processing unit (CPU) according to one embodiment. According to other embodiments, the processor 7 may include other electronic components capable of carrying out processing functions, such as a digital signal processor, a field-programmable gate array (FPGA), a graphics processing unit (GPU), or any other type of processor. According to other embodiments, the processor 7 may include a plurality of electronic components capable of carrying out processing functions. For example, the processor 7 may include two or more electronic components selected from a list of electronic components including: a central processing unit, a digital signal processor, a field-programmable gate array, and a graphics processing unit.

The processor 7 may also include a complex demodulator (not shown) that demodulates RF data. In another embodiment, the demodulation can be carried out earlier in the processing chain.

The processor 7 is adapted to perform one or more processing operations according to a plurality of selectable ultrasonic modalities on the data. The data may be processed in real-time during a scanning session as the echo signals are received. For the purpose of this disclosure, the term "real-time" is defined to include a procedure that is performed without any intentional delay.

The data may be temporarily stored in a buffer (not shown) during ultrasonic scanning, so that they can be processed in a live operation or in an off-line operation not in real-time. In this disclosure, the term "data" may be used in the present disclosure to refer to one or more datasets acquired using an ultrasonic image display apparatus.

The ultrasound data may be processed by the processor 7 in other or different mode-related modules (e.g., B-mode, color Doppler, M-mode, color M-mode, spectral Doppler, contrast-enhanced mode, elastography, TVI, strain, strain rate, and the like) to form data for ultrasonic images. For example, one or more modules may produce ultrasonic images in B-mode, color Doppler, M-mode, color M-mode, spectral Doppler, contrast-enhanced mode, elastography, TVI, strain, strain rate, and combinations thereof, and the like.

The image beams and/or image frames are stored and timing information indicating a time at which the data was acquired in memory may be recorded. The modules may include, for example, a scan conversion module to perform scan conversion operations to convert the image frames from coordinate beam space to display space coordinates. A video processor module may be provided that reads the image frames from memory and displays the image frames in real-time while a procedure is being carried out on the patient. The video processor module may store the image frames in image memory, from which the ultrasonic images are read and displayed on the display 8.

The ultrasound data before the scan conversion operations will be referred to herein as raw data. The data after the scan conversion operations will be referred to herein as image data. The phrase "data for an ultrasonic image" may include both of raw data and image data.

In the case that the processor 7 includes a plurality of processors, the aforementioned processing tasks to be handled by the processor 7 may be handled by the plurality of processors. For example, a first processor may be utilized to demodulate and decimate the RF signal while a second processor may be used to further process the data prior to displaying an image.

In the case that the receive beamformer 6 is a software beamformer, for example, its processing functions may be carried out by a single processor or by a plurality of processors.

The display 8 is an LED (Light Emitting Diode) display, an LCD (Liquid Crystal Display), an organic EL (Electro-Luminescence) display, or the like.

The memory 9 is any known data storage medium. In an example, the ultrasonic image display apparatus 1 comprises non-transitory storage media and transitory storage media as the memory 9, and comprises a plurality of units of memory 9. The non-transitory storage medium is, for example, a non-volatile storage medium such as an HDD (Hard Disk Drive) and ROM (Read Only Memory). The non-transitory storage media may include a portable storage medium such as a CD (Compact Disk) and a DVD (Digital Versatile Disk). Programs executed by the processor 7 are stored in a non-transitory storage medium. In the non-transitory storage medium, protocols, data for first and second ultrasonic images, and information SI1, SI2 are also stored, which will be discussed later. All of them may be stored in the same unit of memory 9, or at least one of them may be stored in a different unit of memory 9.

The transitory storage medium is a volatile storage medium such as RAM (Random Access Memory).

The user interface 10 can accept an operator's input. For example, the user interface 10 accepts an input of a command and/or information from the operator. The user interface 10 is adapted to include a keyboard, hard keys, a trackball, a rotary control, soft keys, and the like. The user interface 10 may include a touch screen that displays soft keys, etc.

The speaker 11 is controlled by the processor 7 to output sound. In an example, the speaker 11 outputs sound based on the signals input from the processor 7.

Next, an operation in the ultrasonic image display apparatus 1 in the present embodiment will be described. Acquisition of an ultrasonic image following a protocol stored in the memory 9 for display will be described hereinbelow with reference to the flow chart in FIG. 2. The protocol includes a plurality of image acquisition steps, and each image acquisition step is executed following the flow chart in FIG. 2 to perform an examination on a patient. At least one of the position and angle of the ultrasonic probe on the surface of the patient may be different for each image acquisition step. Moreover, for each image acquisition step, conditions for ultrasound transmission/reception and/or those for ultrasonic image data creation may be different. The conditions for ultrasound transmission/reception and those for ultrasonic image data creation are stored in the memory 9 for each of the image acquisition steps, and constitute particulars of the protocol.

Figure 2:
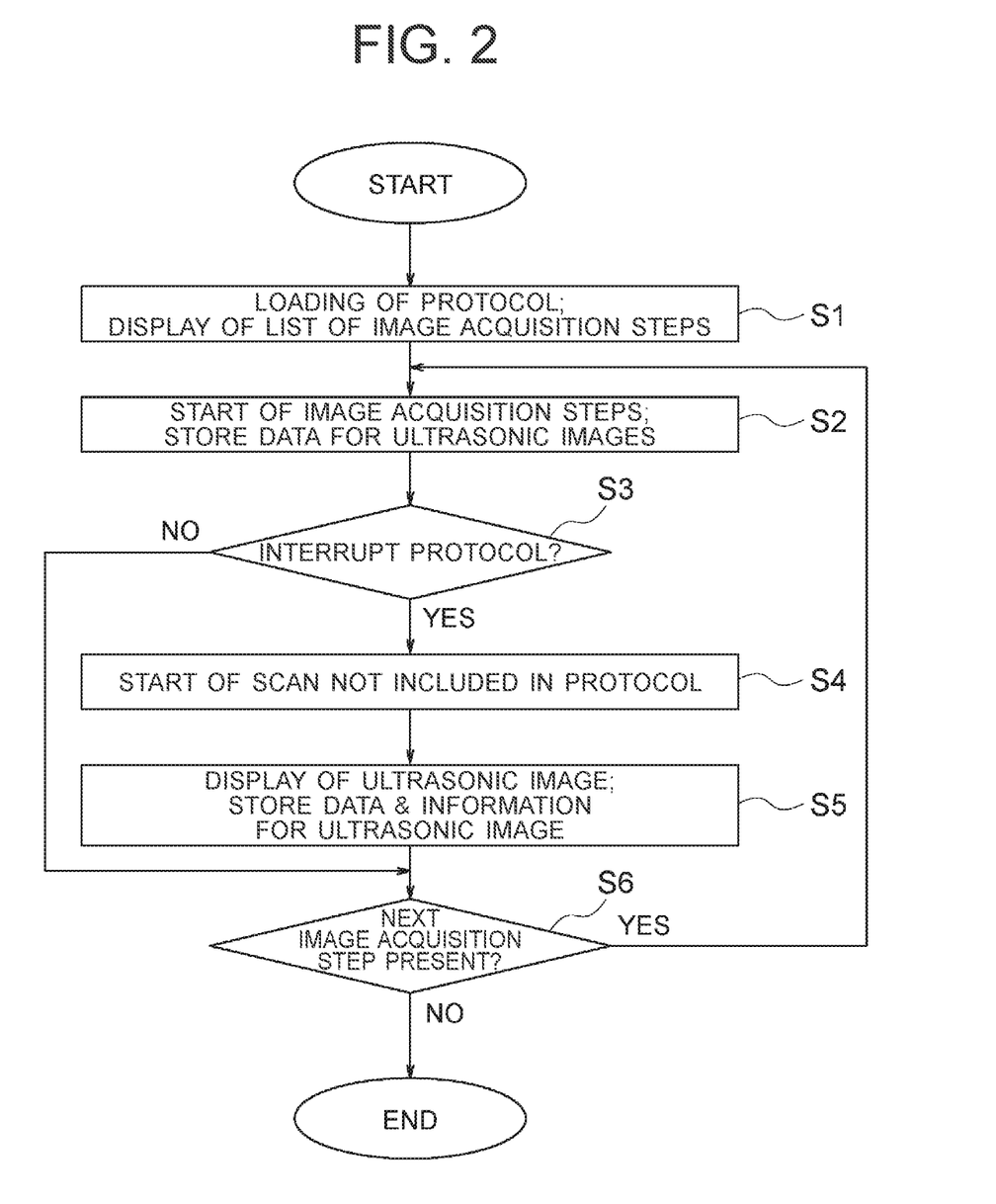
FIG. 2 is a flow chart showing an example of processing in a first run of a protocol in accordance with an embodiment.

A plurality of protocols may be stored in the memory 9. In this case, when the user interface 10 has accepted an operator's input for selecting one of the plurality of protocols, the flow chart in FIG. 2 is initiated to start an examination. The run of the protocol in the flow chart in FIG. 2 is defined herein as a first run.

Figure 3:
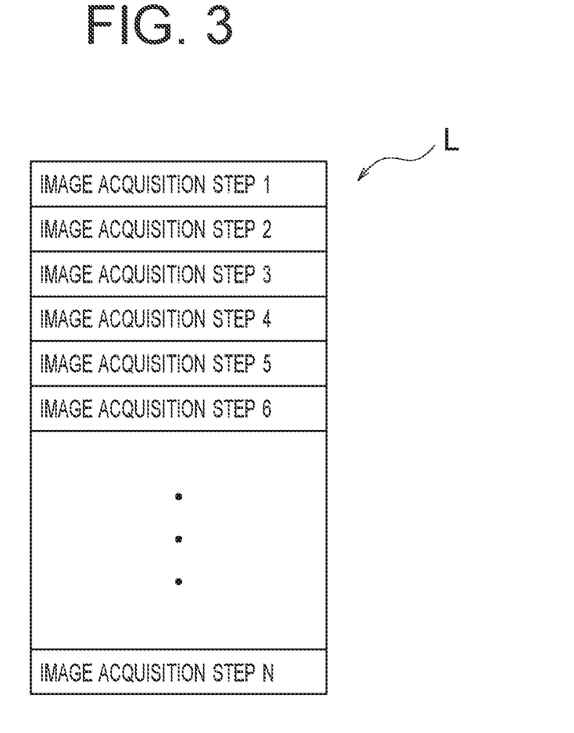
FIG. 3 is a diagram showing an example of a list of image acquisition steps displayed on a display in the first run of the protocol in accordance with the embodiment.

First, at Step S1, the processor 7 loads a protocol from the memory 9, and displays a list L of image acquisition steps included in the protocol on the display 8. FIG. 3 shows an example of the list L of the image acquisition steps. The list L contains image acquisition steps 1 to N.

Next, at Step S2, the processor 7 starts an image acquisition step. Here, a first image acquisition step defined by the protocol is started. The processor 7 controls the ultrasonic probe 2 to transmit/receive ultrasound, and creates data for an ultrasonic image based on resulting echo signals. The processor 7 performs ultrasound transmission/reception and ultrasonic image data creation with conditions defined in the protocol. For example, the conditions include a depth of ultrasonic image display, a transmission frequency, transmission focus and reception focus, a gain, a dynamic range, a filter, and the like.

Moreover, at Step S2, the processor 7 stores acquired data for an ultrasonic image in the memory 9. For example, when the user interface 10 has accepted an operator's input for commanding storing of data for an ultrasonic image, the processor 7 stores data for an ultrasonic image in the memory 9. The memory 9 here is a non-volatile storage medium in an example.

The data for an ultrasonic image acquired at an image acquisition step included in the protocol is defined herein as data for a first ultrasonic image. The data for a first ultrasonic image is stored so that one can recognize that it is acquired in a specific protocol (This applies to data for a second ultrasonic image, and information SI1, SI2), which will be discussed later.

The processor 7 may store information SI1 indicating an ongoing one of the plurality of image acquisition steps in the memory 9. The information SI1 is stored in association with the data for a first ultrasonic image stored in the memory 9. In an example, the data for a first ultrasonic image may be stored in a DICOM (Digital Imaging and Communications in Medicine) format, and the information SI1 may be stored in a DICOM header.

The information SI1 is information specifying each of the plurality of image acquisition steps, and may be numerical, for example. The information SI1 may be an image number of data for an ultrasonic image. In this case, a range of image numbers may be defined for each of the plurality of image acquisition steps, whereby the image number may be used as the information specifying each of the plurality of image acquisition steps. For example, the range of image numbers are defined for each of the plurality of image acquisition steps, such as that the range of image numbers for a first image acquisition step are defined as "100" to "199," the range of image numbers for a second image acquisition step are defined as "200" to "299," and the like. The image number may be stored so that one can recognize that it is assigned in a specific protocol.

It should be noted that the information SI1 cited herein is merely an example, and the information SI1 may be, for example, text information, etc. different from the image number but indicating an image acquisition step.

Next, at Step S3, the processor 7 decides whether or not to interrupt the run of the protocol. The term "interrupt" refers to temporary interruption, in other words, a pause. When the user interface 10 has accepted an operator's input for interrupting the run of the protocol, the processor 7 decides to interrupt the run of the protocol ("YES" at Step S3), where processing moves to Step S4. On the other hand, when the user interface 10 has accepted an operator's input for commanding move to the next image acquisition step, the processor 7 decides not to interrupt the run of the protocol ("NO" at Step S3), where processing moves to Step S6.

At Step S4, the processor 7 controls the ultrasonic probe 2 to start ultrasound transmission/reception not included in the protocol, and creates data for an ultrasonic image. The ultrasonic image data creation after interrupting the run of the protocol implies that data for an ultrasonic image deviating from the image acquisition step included in the protocol, in other words, data for a deviatoric image, is acquired. The data for a deviatoric image is defined herein as data for a second ultrasonic image.

When the operator interrupts the run of the protocol to acquire data for a second ultrasonic image deviating from an image acquisition step, the operation implies that the operator has found an observation of concern, such as that a portion targeted by the first ultrasonic image acquired at an image acquisition step immediately before interruption is a suspicious lesion, etc., for example. The second ultrasonic image may be regarded as an image for observing an object under observation in more detail, in an example.

The conditions for ultrasound transmission/reception and those for second ultrasonic image data creation at Step S4 may include different conditions from those included in the image acquisition step immediately before interruption. In an example, conditions for acquiring data for a second ultrasonic image may be set in response to an operator's input of conditions at the user interface 10.

For example, the data for a second ultrasonic image may be created based on echo signals obtained with a changed angle of the ultrasonic probe 2 as compared with that before interruption of the protocol. In the case that the ultrasonic image before interruption is a still image, video data for a second ultrasonic image may be created.

At Step S5, the processor 7 displays an ultrasonic image based on the data for a second ultrasonic image on the display 8, and stores the data in the memory 9. The processor 7 also stores information SI2 in the memory 9. Again, the memory 9 here is a non-volatile storage medium in an example. When the user interface 10 has accepted an operator's input for performing storing of the data for a second ultrasonic image, the processor 7 executes storing in the memory 9.

The information SI2 at least indicates that the first run of the protocol is interrupted at a specific one of the plurality of image acquisition steps. The information SI2 may be information indicating that the first run of the protocol is interrupted at a specific one of the plurality of image acquisition steps, and moreover the information specifying the second ultrasonic image. In the case that a plurality of protocols are stored in the memory 9, the information SI2 may include information indicating a specific one of the plurality of protocols.

The information SI2 may be stored in association with the data for a second ultrasonic image. Again, the data for a second ultrasonic image may be stored in a DICOM format, and the information SI2 may be stored in a DICOM header in an example.

For example, the processor 7 may store an image number as the information SI2, as with the information S1. In an example, in the case that the image number is a 3-digit number as described earlier, the processor 7 may assign as the information SI2 an image number whose tens place is modified from that assigned to the data for a first ultrasonic image stored immediately before interruption. Specifically, in the case that the image number assigned to the data for a first ultrasonic image stored immediately before interruption is "100," the data for a second ultrasonic image stored after interruption is assigned with an image number of "110". An image number ranging from "100" to "109" indicates the data for a first ultrasonic image, while an image number after "110" indicates the data for a second ultrasonic image. However, all that is needed is to define a range of image numbers assigned to the data for a first ultrasonic image and those assigned to the data for a second ultrasonic image at a specific image acquisition step, and the aforementioned example of assignment of the image number is merely an example. The image number may be assigned so that one can recognize that it is assigned in a specific protocol.

At Step S5, the processor 7 may store the conditions used for acquiring the data for a second ultrasonic image in the memory 9 in association with the data for a second ultrasonic image. The processor 7 may execute storing of the aforementioned conditions when the user interface 10 has accepted an operator's input for performing storing of the data for a second ultrasonic image.

Next, at Step S6, the processor 7 decides whether or not a next image acquisition step is present in the protocol. In the case that the next image acquisition step is decided to be present ("YES" at Step S6), processing returns to Step S1 to start the next image acquisition step. In the case that the first run of the protocol has been interrupted at Step S3, the first run is resumed by starting the next image acquisition step. On the other hand, in the case that the next image acquisition step is decided not to be present ("NO" at Step S6), the first run of the protocol ends, and the examination is terminated.

Additionally, when the protocol is executed, a history of the run of the protocol for the specific patient may be stored in the memory 9.

Figure 4:
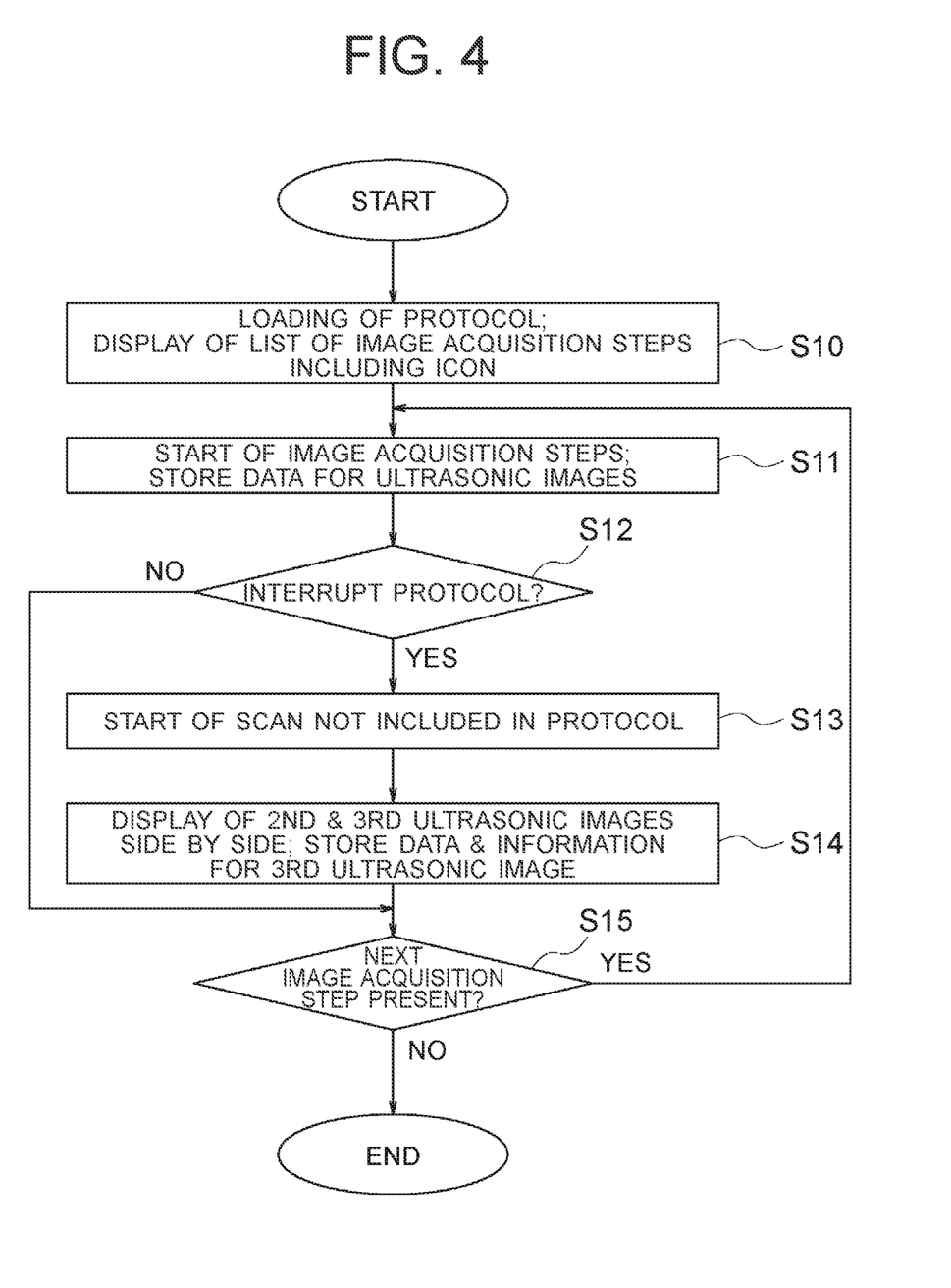
FIG. 4 is a flow chart showing an example of processing in the first run of the protocol in accordance with the embodiment.

Next, processing of executing the same protocol after the first run of the protocol ends will be described with reference to the flow chart in FIG. 4. The run of the protocol in the flow chart in FIG. 4 is defined herein as a second run.

The second run of the protocol is performed after the first run of the protocol has ended following FIG. 2. For example, the second run of the protocol is performed for acquiring an ultrasonic image for the purpose of subsequent observation of the condition, etc. of the patient for whom the first ultrasonic image and second ultrasonic image were acquired in the first run of the protocol. For example, when the user interface 10 has accepted an operator's input for selecting a protocol, the second run of the protocol is initiated. It is assumed here that the same protocol as that executed following FIG. 2 is selected.

The processor 7 may decide whether or not the selected protocol was performed on the same patient in the past based on the history of the run of the protocol. In the case that the processor 7 decides that the selected protocol was performed on the same patient in the past, it performs a second run of the protocol following the flow chart in FIG. 4.

It is assumed here that in the memory 9 are stored the data for a first ultrasonic image acquired at each of the plurality of image acquisition steps by the first run of the protocol, and the data for a second ultrasonic image acquired while interrupting the protocol at one of the image acquisition steps.

Figure 5:
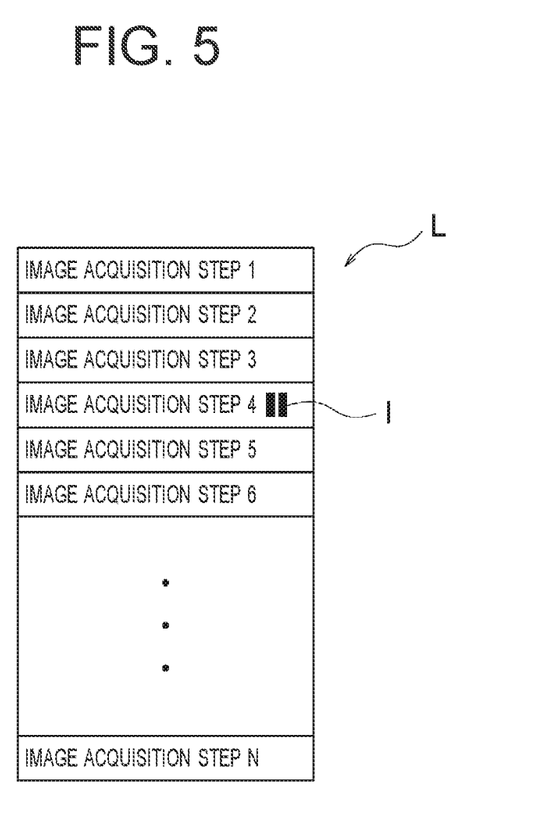
FIG. 5 is a diagram showing an example of the list of image acquisition steps displayed on the display in a second run of the protocol in accordance with the embodiment.

In the flow chart in FIG. 4, first, at Step S10, the processor 7 loads the protocol and information SI2 from the memory 9. The processor 7 also displays the list L of the image acquisition steps on the display 8, as in Step S1. It should be noted that at Step S10 here, the processor 7 displays an icon I in the list L, as shown in FIG. 5.

The icon I gives notice to the operator or the like that the second run of the protocol will be interrupted at the same image acquisition step as that specified by the information SI2. The icon I also indicates the same image acquisition step as that at which the first run of the protocol was interrupted. The processor 7 displays the icon I at the image acquisition step specified by the information SI2 loaded from the memory 9. In FIG. 5, the icon I is displayed at "Image acquisition step 4," which indicates that the first run of the protocol was interrupted at the "Image acquisition step 4."

It should be noted that the icon I is merely an example, and the image acquisition steps may be distinguished from one another by a display manner instead of the icon I, such as, for example, that text of the image acquisition step at which the first run of the protocol was interrupted is displayed in a color different from that of other image acquisition steps.

At Step S11, the same processing as Step S2 is performed and data for an ultrasonic image is stored. The data for the ultrasonic image acquired at the image acquisition step in the second run of the protocol is also defined herein as data for a first ultrasonic image.

At Step S12, the processor 7 decides whether or not to interrupt the second run of the protocol. In an example, as in Step S3, the processor 7 may decide to interrupt the second run of the protocol once the user interface 10 has accepted an operator's input for interrupting the run of the protocol ("YES" at Step S12). In the case that the image acquisition step started at Step S11 is the one at which the icon I is displayed in the list L, the operator performs an input for interrupting the second run of the protocol at the user interface. On the other hand, when the user interface 10 has accepted an operator's input for commanding moving to the next image acquisition step, it decides not to interrupt the second run of the protocol ("NO" at Step S12), and processing moves to Step S15.

In the case that the image acquisition step started at Step S11 is the same as that specified by the information SI2, text or the like indicating that the second run of the protocol should be interrupted, such as, for example, "Interrupt the second run of the protocol," etc., may be displayed on the display 8. Moreover, in the case that the image acquisition step started at Step S11 is the same as that specified by the information SI2, sound may be output from the speaker 11. The sound indicates that the image acquisition step started at Step S11 is the image acquisition step at which the first run of the protocol was interrupted, or the second run of the protocol should be interrupted. The processor 7 outputs a signal to the speaker 11, based on which the sound is output. Once the sound has been output, the operator performs an input for interrupting the second run of the protocol.

The sound output from the speaker 11 may be an alarm sound, for example. Moreover, the sound output from the speaker 11 may be a voice giving notice that the image acquisition step started at Step S11 is the same as that at which the first run of the protocol was interrupted or commanding that the second run of the protocol should be interrupted.

In the case that the sound described above is output from the speaker 11, it is not necessary to display the icon I at Step S11.

By the icon I or the like being displayed on the display 8 or the sound being output from the speaker 11, the operator can recognize the image acquisition step interrupted during the first run of the protocol in the past. The operator can thus interrupt the second run of the protocol without fail at the same image acquisition step as that at which the first run of the protocol was interrupted.

At Step S12, in another example, the processor 7 may decide whether or not to interrupt the second run of the protocol based on the information SI2. Specifically, in the case that the image acquisition step started at Step S11 is the one specified by the information SI2, the processor 7 decides to interrupt the second run of the protocol ("YES" at Step S12). On the other hand, in the case that the image acquisition step started at Step S11 is not the one specified by the information SI2, the processor 7 decides not to interrupt the second run of the protocol ("NO" at Step S12).

In the case that the processor 7 is configured to make a decision not based on the operator's input but on the information SI, display of the icon I or output of sound from the speaker 11 is not necessary.

In the case that the second run of the protocol is decided to be interrupted, processing moves to Step S13. At Step S13, the processor 7 controls the ultrasonic probe 2 to start ultrasound transmission/reception not included in the protocol, and creates data for an ultrasonic image, as in Step S4.

The data for an ultrasonic image acquired while interrupting the second run of the protocol is defined herein as data for a third ultrasonic image.

Conditions for ultrasound transmission/reception and those for third ultrasonic image data creation at Step S13 may be those used for acquiring the data for a second ultrasonic image in the first run of the protocol and stored in the memory 9. The processor 7 loads the data for a second ultrasonic image from the memory 9 based on the information SI2, and moreover loads the conditions used for creating the data for a second ultrasonic image from the memory 9 and sets them. Thus, data for a third ultrasonic image can be acquired without the operator setting the conditions. Timing for loading the conditions from the memory 9 is, however, not limited to Step S13, and may be Step S10, for example.

Figure 6:
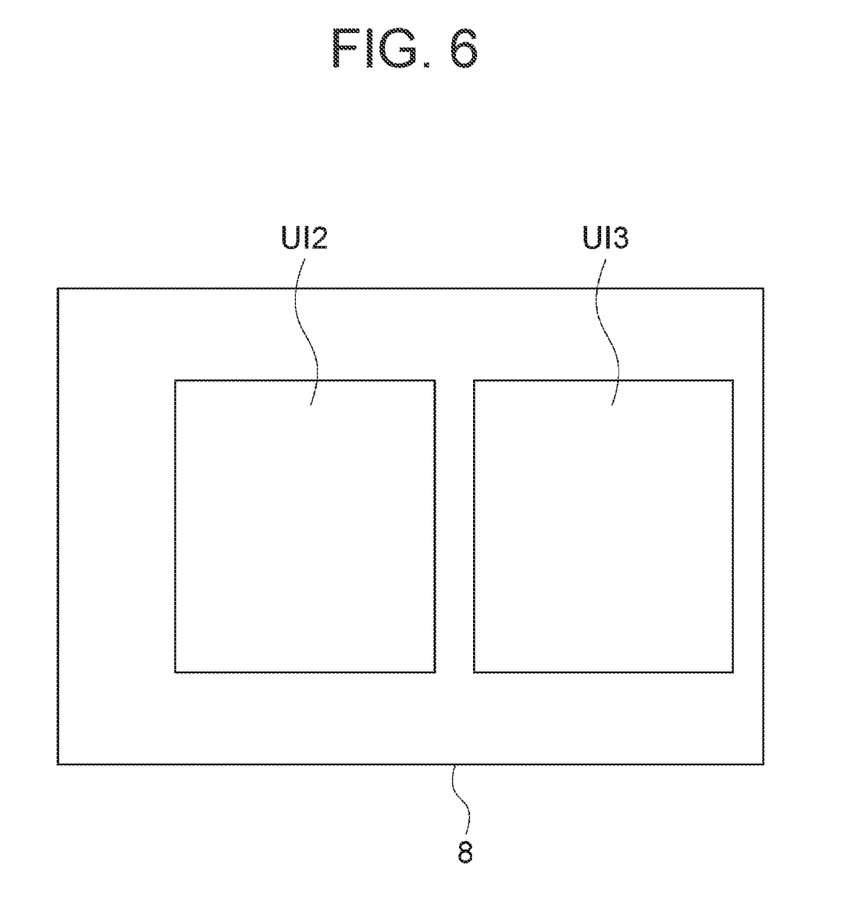
FIG. 6 is a diagram showing the display on which a second ultrasonic image acquired in the second run of the protocol and that acquired in the first run of the protocol are displayed side by side.

At Step S14, the processor 7 displays the third ultrasonic image (real-time image) based on the data for a third ultrasonic image on the display 8, and stores the data for a third ultrasonic image and information SI2 in the memory 9, as in Step S5. Again, the memory 9 here is a non-volatile storage medium, in an example. Moreover, the processor 7 may display the second ultrasonic image stored in the memory 9 in the first run of the protocol on the display 8. The processor 7 may display the second ultrasonic image UI2 and third ultrasonic image UI3 side by side on the display 8 for facilitating comparison by the operator, as shown in FIG. 6. Since the operator is not required to perform an operation for displaying the second ultrasonic image UI2, (s)he can easily display the image for comparison with the third ultrasonic image UI3.

It should be noted that timing at which the processor 7 loads the data for a second ultrasonic image stored in the first run of the protocol is not limited to Step S14, and may be Step S10, for example.

Next, at Step S15, the processor 7 decides whether or not a next image acquisition step is present in the protocol, as in Step S6. In the case that the next image acquisition step is present ("YES" at Step S15), processing returns to Step S10 to resume the second run. On the other hand, in the case that the next image acquisition step is not present ("NO" at Step S15), the second run of the protocol is terminated.

For example, in the case that measurement is performed in the second ultrasonic image at Step S5, the information SI2 may include information specifying a kind of measurement. In an example, the size of the object under observation is measured in the second ultrasonic image. In this case, at Step S14, the processor 7 may display graphics on the display 8 for performing the measurement specified by the information SI2 on the third ultrasonic image.

Figure 7:
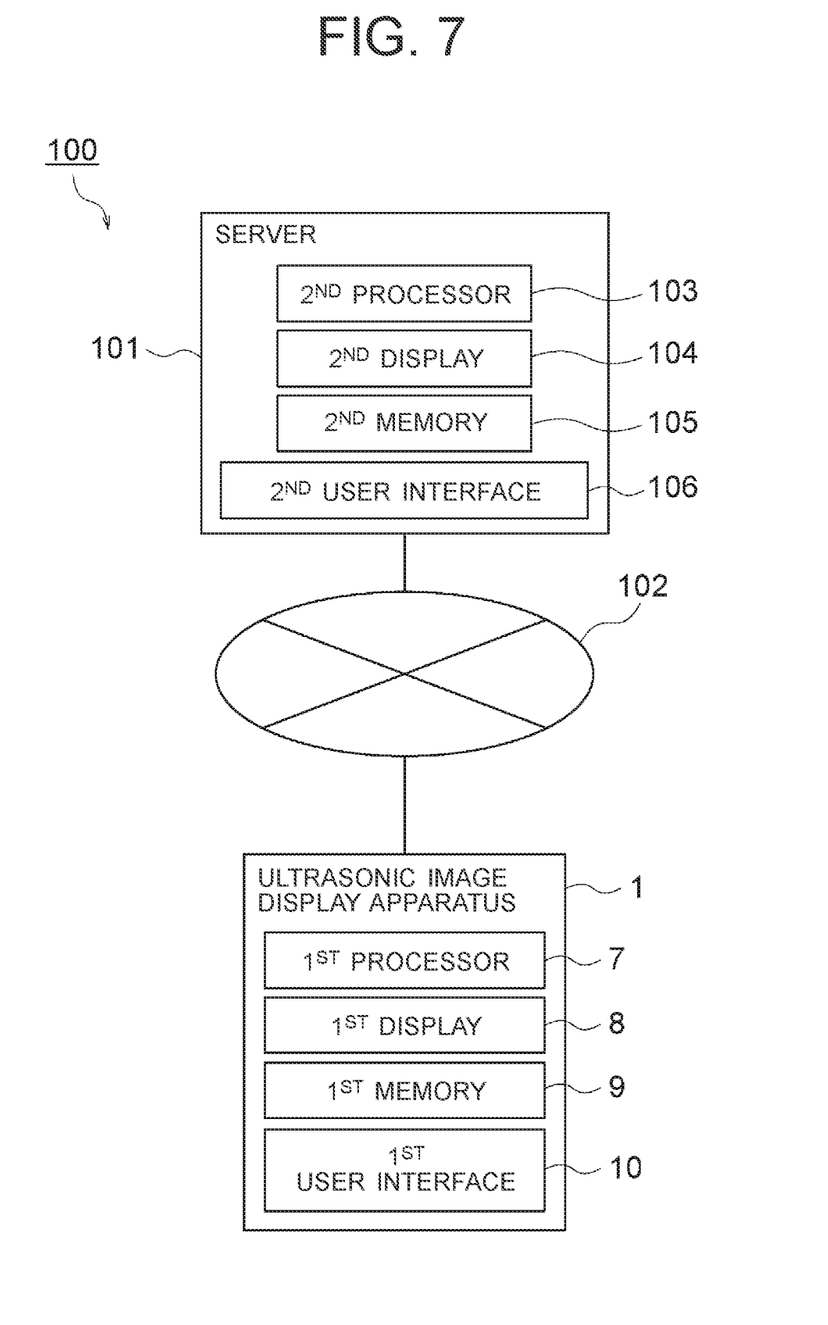
FIG. 7 is a block diagram showing another example of the ultrasonic image display system.

While the ultrasonic image display apparatus has been described as an example of the ultrasonic image display system in the embodiments above, the ultrasonic image display system 100 may be constructed to comprise the ultrasonic image display apparatus 1 and a server 101, as shown in FIG. 7.

The ultrasonic image display apparatus 1 and server 101 are connected with each other via a network 102. The ultrasonic image display apparatus 1 has the same configuration as FIG. 1. In FIG. 7, however, the processor 7, display 8, memory 9, and user interface 10 in the ultrasonic image display apparatus 1 are described as a first processor 7, a first display 8, first memory 9, and a first user interface 10. While only the first processor 7, first display 8, first memory 9, and first user interface 10 are shown as components of the ultrasonic image display apparatus 1 in FIG. 7, the ultrasonic image display apparatus 1 has additional components, such as the ultrasonic probe 2, shown in FIG. 1. In FIG. 7, the components are merely shown as blocks.

The server 101 has publicly known components of a server, and has a second processor 103, a second display 104, second memory 105, and a second user interface 106.

In the ultrasonic image display system 100, again, processing is performed following the flow chart shown in FIG. 2. However, a main component and other components performing the processing are different from the embodiments above. Now matters different from the embodiments above will be described below.

According to various embodiments, in the first run of the protocol, at Step S2, the data for a first ultrasonic image and information SD may be stored in the second memory 105 in the server 101. Moreover, at Step S5, the data for a second ultrasonic image and information SI2 may be stored in the second memory 105 in the server 101. Furthermore, the data for first and third ultrasonic images acquired in the second run of the protocol may also be stored in the second memory 105 in the server 101.

In the second run of the protocol, the second processor 103 may load the information SI2 from the second memory 105 in the server 101 at Step S10 in response to the user interface 10 in the ultrasonic image display apparatus 1 accepting an input. The information SI2 loaded from the second memory 105 is input to the ultrasonic image display apparatus 1 via the network 102, and is used in the second run of the protocol in the ultrasonic image display apparatus 1.

The second ultrasonic image displayed at Step S14 may be of the data for a second ultrasonic image loaded from the second memory 105 in the server 101.

Moreover, the embodiments above may be implemented as a method of controlling an ultrasonic image display system comprising at least one processor, and memory, wherein
 a. in said memory is stored at least one protocol including a plurality of image acquisition steps, each of which defines conditions for acquiring a first ultrasonic image of a patient, and
 b. said method of controlling is for the processor to perform control comprising the acts of:
 i. loading said protocol from said memory to start a first run of said protocol on said patient;
 ii. after starting the first run of said protocol, interrupting the first run of said protocol at one of said plurality of image acquisition steps;
 iii. after interruption of the first run of said protocol, acquiring data for a second ultrasonic image of said patient and storing the data in said memory, and moreover storing in said memory information indicating that the first run of said protocol is interrupted at the specific one of said plurality of image acquisition steps;
 iv. after resuming the first run of said protocol and completing said run, and when starting a second run of said protocol on said patient, loading said information from said memory; and
 v. giving notice that the second run of said protocol will be interrupted at the same image acquisition step as that specified by said information.

The embodiments above may also be implemented as a method of controlling an ultrasonic image display system comprising at least one processor, memory, and a display, wherein
 a. in said memory is stored at least one protocol including a plurality of image acquisition steps, each of which defines conditions for acquiring a first ultrasonic image of a patient, and
 b. said method of controlling is for the processor to perform control comprising the acts of:
 i. loading said protocol from said memory to start a first run of said protocol on said patient;
 ii. after starting the first run of said protocol, interrupting the first run of said protocol at one of said plurality of image acquisition steps;
 iii. after interruption of the first run of said protocol, acquiring data for a second ultrasonic image of said patient and storing the data in said memory, and moreover storing in said memory information indicating that the first run of said protocol is interrupted at the specific one of said plurality of image acquisition steps, and moreover said information specifying said second ultrasonic image;
 iv. after resuming the first run of said protocol and completing said run, and when starting a second run of said protocol on said patient, loading said information from said memory;
 v. interrupting the second run of said protocol at said image acquisition step specified by said information; and
 vi. loading from said memory the data for said second ultrasonic image specified by said information and displaying said second ultrasonic image on said display.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. An ultrasonic imaging system, the imaging system comprising: a memory storing instructions including at least one protocol comprising a plurality of image acquisition steps, each of the plurality of image acquisition steps defining conditions for acquiring a first ultrasonic image of a patient; at least one processor configured to execute the instructions to: control a transducer of the ultrasonic system to image the patient based on said at least one protocol to perform a first run of said protocol; after starting the first run of said protocol, interrupt the first run of said protocol at one of said plurality of image acquisition steps; after interruption of the first run of said protocol, control the transducer to acquire data for a second ultrasonic image of said patient and storing the data in said memory, and storing in said memory information indicating that the first run of said protocol is interrupted at the specific one of said plurality of image acquisition steps; after completing said first run, control the transducer to image the patient based on said protocol to perform a second run of said protocol, when starting a second run of said protocol on said patient, load said information indicating that the first run of said protocol is interrupted at the specific one of said plurality of image acquisition steps from said memory; and control the ultrasound imaging system to interrupt the second run of said protocol at the same image acquisition step as that specified by said information indicating that the first run of said protocol is interrupted at the specific one of said plurality of image acquisition steps.

2. The ultrasonic imaging system as recited in claim 1, wherein:
said memory further stores therein conditions used for acquiring the data for said second ultrasonic image in association with the data for said second ultrasonic image, and
said at least one processor being further configured to:
load from said memory the conditions used for acquiring the data for said second ultrasonic image specified by said information, and
control the transducer to acquire a third ultrasonic image using the conditions loaded from said memory after interrupting the second run of said protocol.

3. The ultrasonic imaging system as recited in claim 2, wherein: said at least one processor is configured to execute the instructions to control a display of the ultrasonic imaging statem to displays said second ultrasonic image and said third ultrasonic image side by side on said display.

4. The ultrasonic imaging system as recited in claim 1, further comprising:
a user interface for accepting an operator's input, wherein said at least one processor is configured to execute the instructions to interrupt interrupt the first run of said protocol based on the operator's input.

5. The ultrasonic image display system as recited in claim 1, further comprising:
a display, wherein
an act of interrupting the second run of said protocol comprises at least one of: displaying on said display the notice that the second run of said protocol will be interrupted at the same image acquisition step as that specified by said information; and displaying on said display the same image acquisition step as that at which the first run of said protocol was interrupted.

6. The ultrasonic image display system as recited in claim 1, further comprising:
a speaker, wherein
an act of interrupting the second run of said protocol comprises at least one of: outputting from said speaker by a sound the notice that the second run of said protocol is interrupted at the same image acquisition step as that specified by said information; and outputting from said speaker by a sound the same image acquisition step as that at which the first run of said protocol was interrupted.

7. The ultrasonic image display system as recited in claim 1, wherein:
said at least one protocol is a plurality of protocols, and said information indicating that the first run of said protocol is interrupted at the specific one of said plurality of image acquisition steps includes information representing a specific one among said plurality of protocols.

8. The ultrasonic image display system as recited in claim 1, wherein: said at least one protocol is a plurality of protocols, and said information indicating that the first run of said protocol is interrupted at the specific one of said plurality of image acquisition steps includes information representing a specific one among said plurality of protocols.

9. The ultrasonic image display system as recited in claim 1, wherein:
said second ultrasonic image is acquired using different conditions from those included in the image acquisition step immediately before interruption.

10. The ultrasonic image display system as recited in claim 1, wherein:
said second ultrasonic image is acquired using different conditions from those included in an image acquisition step immediately before interruption.

11. The ultrasonic image display apparatus as recited in claim 2, wherein:
said information includes a kind of measurement performed on said second ultrasonic image, and
said at least one processor is configured to execute the instruction to display on a display graphics for performing the measurement specified by said information on said third ultrasonic image.

12. The ultrasonic image display apparatus as recited in claim 1, wherein: said memory is a non-volatile storage medium.

13. A non-transitory computer readable medium storing a program for controlling an ultrasonic imaging system comprising at least one processor, a transducer, and memory, wherein
in said memory is stored at least one protocol including a plurality of image acquisition steps, each of which defines conditions for acquiring a first ultrasonic image of a patient, and
said program for controlling causes said processor to perform control comprising the acts of:
controlling the transducer to image the patient based on said at least one protocol to perform a first run of said protocol on said patient;
after starting the first run of said protocol, interrupting the first run of said protocol at one of said plurality of image acquisition steps;
after interruption of the first run of said protocol, controlling the transducer to acquire data for a second ultrasonic image of said patient and storing the data in said memory, and storing in said memory information indicating that the first run of said protocol is interrupted at the specific one of said plurality of image acquisition steps;
after completing said first run, controlling the transducer to image the patient based on said protocol to perform a second run of said protocol, when starting a second run of said protocol on said patient, loading said information indicating that the first run of said protocol is interrupted at the specific one of said plurality of image acquisition steps from said memory; and
controlling the ultrasonic imaging system to interrupt the second run of said protocol at the same image acquisition step as that specified by said information indicating that the first run of said protocol is interrupted at the specific one of said plurality of image acquisition steps.

\* \* \* \* \*